May 6, 1969 F. W. ANDERSON Plant Pat. 2,883
NECTARINE TREE
Filed Oct. 30, 1967
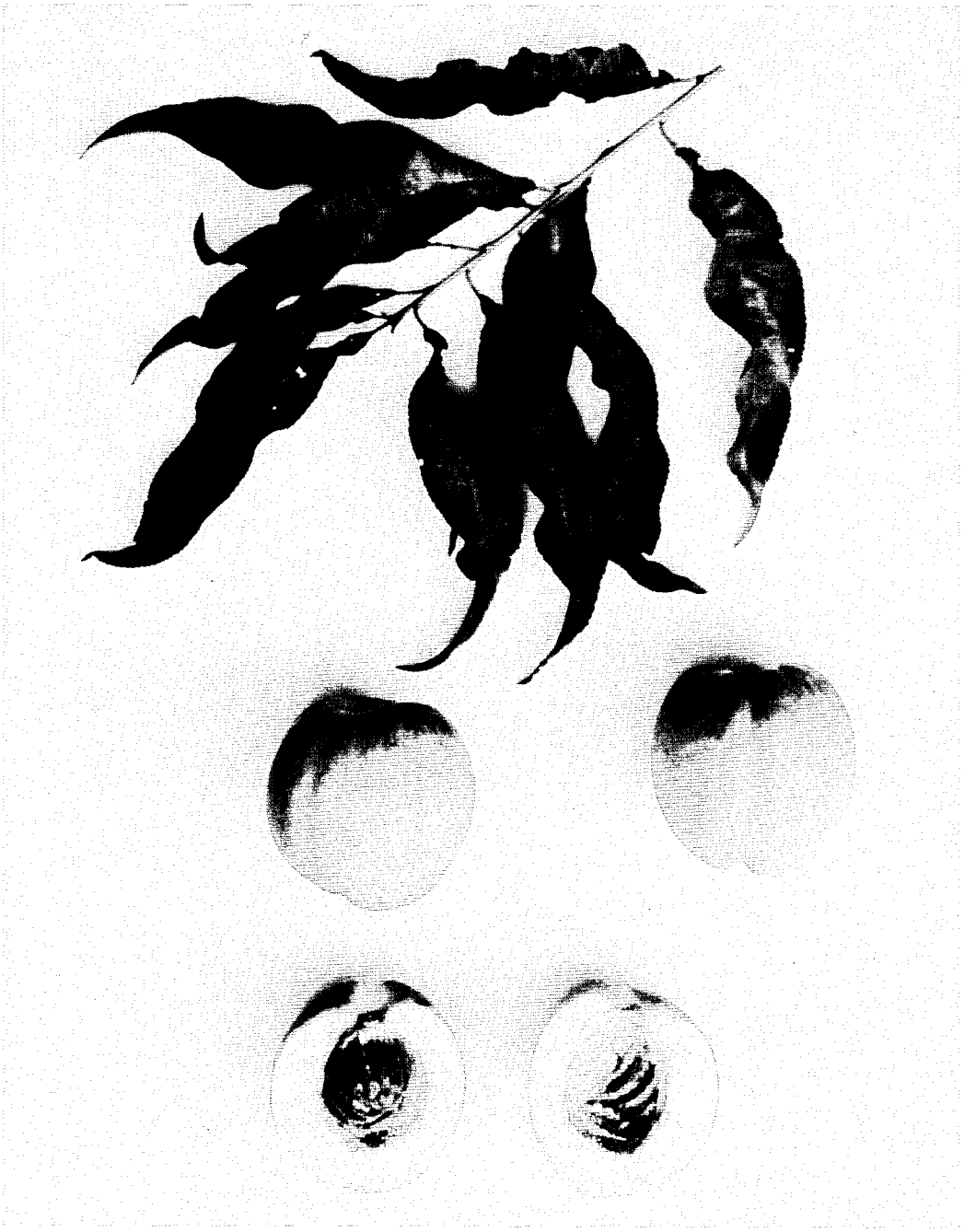
INVENTOR
Frederic W. Anderson
BY Webster & Webster
ATTORNEYS

United States Patent Office

Plant Pat. 2,883
Patented May 6, 1969

2,883
NECTARINE TREE

Frederic W. Anderson, Merced, Calif., assignor to Reedley Nursery, Inc., Reedley, Calif., a corporation of California Filed Oct. 30, 1967, Ser. No. 679,272
Int. Cl. A01h *5/08*
U.S. Cl. Plt.—41 1 Claim

ABSTRACT OF THE DISCLOSURE

A large, vigorous nectarine tree which is a regular and productive bearer of large, globose to slightly oblong, freestone fruit having yellow flesh, and yellow skin substantially entirely overspread with red at maturity.

*Classification of the variety*

The variety is embraced by Group 111 (with bitter kernels) of the classification established by Caillavet and Souty in their Monographie des Principales Variétés de Pêchers, 1950 edition, at page 46.

*Background of the variety*

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

*Origin of the variety*

The present variety of nectarine tree was originated by me in my experimental orchard, located as aforesaid, as a first generation cross between the Red Grand nectarine (United States Plant Patent No. 1,060) and the Early Sun Grand nectarine (United States Plant Patent No. 1,420). When, upon bearing fruit, the original tree of the instant variety—which tree was maintained under close observation by me—evidenced certain characteristics which made it suitable and desirable for commercial growing, I selected it for asexual reproduction.

*Asexual reproduction of the variety*

Subsequent to origination of the variety, as above, I asexually reproduced it by top-working on mature peach trees in my aforementioned orchard. In maturity, all of such reproductions ran true to the original tree in all respects.

*Summary of the variety*

The present variety is characterized by a large, vigorous tree which is a regular and productive bearer of large, globose to slightly oblong, freestone fruit having yellow flesh and yellow skin substantially entirely overspread with red at maturity; the variety being distinctive in that such freestone fruit ripens during approximately the same period as the Le Grand clingstone nectarine (United States Plant Patent No. 549) and the Elberta freestone peach (unpatented).

*Brief description of the drawing*

The drawing is an illustration, by photographic reproduction in color, of fruit of the variety, together with a twig with leaves; the view including one fruit cut in half in the suture plane, with the stone remaining in one half.

*Description of the variety*

The botanical details of this new and distinct variety of nectarine tree—with color definitions (except those in common color terms) referenced to Maerz and Paul Dictionary of Color—are as follows:

Tree:
- *Size.*—Large.
- *Vigor.*—Vigorous.
- *Growth.*—Spreading.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Red to green.

Leaves:
- *Size.*—Large to medium. Average length—4¾". Average width—1⅛".
- *Form.*—Lanceolate; acutely pointed.
- *Thickness.*—Medium.
- *Margin.*—Crenate.
- *Petiole.*—Medium length; medium thickness.
- *Glands.*—Number and position—usually 2 on blade, and 2 to 4 on petiole. Medium size; reniform.
- *Color.*—Top side—medium green (23–L–7). Under side—lighter green (21–L–7).

Flower buds:
- *Size.*—Medium.
- *Length.*—Medium.

Flowers:
- *Blooming period.*—Date of first bloom—Mar. 7, 1967. Date of full bloom—Mar. 25, 1967. Medium, as compared with other varieties.
- *Size.*—Large.
- *Color.*—Pink.

Fruit:
- *Maturity when described.*—Eating ripe—Aug. 18, 1967.
- *Size.*—Uniform; large. Average diameter axially—2½". Average transversely in suture plane—2⅜".
- *Form.*—Uniform; symmetrical; globose to slightly oblong.
- *Suture.*—Distinct; shallow.
- *Ventral surface.*—Rounded slightly.
- *Cavity.*—Rounded.
- *Base.*—Rounded.
- *Apex.*—Short to depressed.

Skin:
- *Thickness.*—Medium.
- *Texture.*—Medium.
- *Tendency to crack.*—None in dry season.
- *Down.*—Wanting.
- *Color.*—Yellow (11–L–6) substantially entirely overspread with red (4–L–4) mottled and streaked dark red (6–L–6), at maturity.

Flesh:
- *Amygdalin.*—Scant.
- *Texture.*—Firm; meaty.
- *Fibers.*—Fine.
- *Ripens.*—Evenly.
- *Flavor.*—Subacid.
- *Eating quality.*—Good.
- *Color.*—Yellow (9–L–5). Surface of pit cavity—red (5–L–4).

Stone:
- *Type.*—Free.
- *Size.*—Medium. Average length—1¼". Average breadth—1". Average thickness—¾".
- *Form.*—Oblong.
- *Sides.*—Equal.
- *Ridges.*—Rounded.

Stone:—Continued

*Tendency to split.*—Slight.

*Kernel.*—Bitter.

*Color.*—Brown (8–H–11).

Use: Market; dessert; long distance shipping.

Keeping quality: Good.

Shipping quality: Good.

The nectarine tree and its fruit herein described may vary in slight detail due to climatic and soil conditions under which the variety may be grown; the present description being of the variety as grown in the Central Valley of California, and wherein in 1967 all fruit ripened over two weeks later than normal.

I claim:

1. A new and distinct variety of nectarine tree, substantially as illustrated and described, which is large, vigorous, and a regular and productive bearer of large, globose to slightly oblong, freestone fruit having yellow flesh, and yellow skin substantially entirely overspread with red at maturity; the fruit ripening approximately with the Le Grand clingstone nectarine.

No references cited.

ROBERT E. BAGWILL, *Primary Examiner.*